United States Patent [19]

Kroposki et al.

[11] 4,016,225
[45] Apr. 5, 1977

[54] PROCESS FOR PREPARING PHOSPHOROTHIOATES AND PHENYLPHOSPHONOTHIOATES

[75] Inventors: Lorraine M. Kroposki, Walnut Creek, Calif.; Masao Yoshimine, Midland, Mich.

[73] Assignee: The Dow Chemical Company, Midland, Mich.

[22] Filed: July 31, 1975

[21] Appl. No.: 600,543

Related U.S. Application Data

[60] Division of Ser. No. 361,937, May 21, 1973, Pat. No. 3,907,815, which is a continuation-in-part of Ser. No. 187,139, Oct. 6, 1971, abandoned.

[52] U.S. Cl. .............................................. 260/973
[51] Int. Cl.² ..................... C07C 9/165; C07C 9/40
[58] Field of Search ................................... 260/973
[56] References Cited
UNITED STATES PATENTS 3,689,602  9/1972  Ismail ........................... 260/973 X

*Primary Examiner*—Anton H. Sutto
*Attorney, Agent, or Firm*—L. Wayne White

[57] ABSTRACT

Mixtures of (1) a quaternary ammonium salt(s) and (2) 1,4-diazabicyclo[2.2.2]octane are novel catalysts in the process of reacting an alkali metal phenate, pyridinate or pyrimidiate with an O,O-dialkyl phosphorochloridothioate or O-alkyl phenylphosphonochloridothioate to produce the corresponding phosphorothioates and phenylphosphonothioates. The process is conducted under alkaline conditions in a liquid reaction medium. As an example, O,O-diethyl 0-(3,5,6-trichloro-2-pyridyl)phosphorothioate is prepared in excellent yields and purity by reacting sodium 3,5,6-trichloropyridinate with O,O-diethyl phosphorochloridothioate in a stirred methylene chloride-water reaction medium in the presence of a catalytic amount of benzyltriethylammonium chloride and 1,4-diazabicyclo[2.2.2]octane.

15 Claims, No Drawings

PROCESS FOR PREPARING PHOSPHOROTHIOATES AND PHENYLPHOSPHONOTHIOATES

CROSS-REFERENCE TO RELATED APPLICATION

This is a divisional of our U.S. patent application Ser. No. 361,937 filed May 21, 1973, now U.S. Pat. No. 3,907,815 which in turn is a continuation-in-part of U.S. patent application Ser. No. 187,139, filed Oct. 6, 1971, now abandoned.

BACKGROUND OF THE INVENTION

The O-pyridyl phosphates and phosphorothioates were described by Rigterink in U.S. Pat. No. 3,244,586. Such compounds are particularly useful as insecticides and biocides. They are represented by Formula (I)

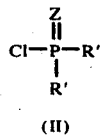

(I)

wherein R represents halopyridyl, Z represents oxygen or sulfur and each R' independently represents lower alkyloxy, amino or lower alkylamino. Rigterink disclosed several methods for preparing the compounds but his preferred method comprised reacting a phosphorochloridate or phosphorochloridothioate of Formula (II)

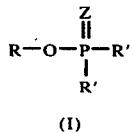

(II)

with an alkali metal or tertiary amine salt of a halopyridinol having the formula R—O—alkali metal or R—OH·tertiary amine. The disclosed methods were carried out in an inert organic liquid under anhydrous conditions. In each of the disclosed processes an alkali metal chloride or the tertiary amine hydrochloride salt is produced as a reaction by-product which is removed by filtration. The disclosure of U.S. Pat. No. 3,244,586 is incorporated herein by reference.

Other phosphorothioates and phenylphosphonothioates have been similarly prepared and used. See, for example, the articles by O. Johnson in Chemical Week, pages 18–46 (26 July 1972) and by E. E. Kenaga and W. E. Allison in the *Bulletin of the Entomological Society of America*, Vol. 15, No. 2, pages 85–148 (June, 1969) which list many commercially available phosphorothioates and phenylphosphonothioates and which include U.S. patents pertaining to such compounds.

The phosphorothioates and phenylphosphonothioates referred to above and herein prepared correspond to the formula

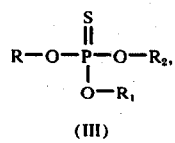 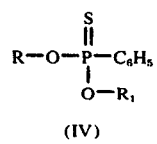

(III)  (IV)

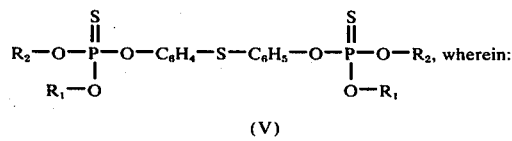

(V)

$R_1$ and $R_2$ are each independently lower alkyl; and R is

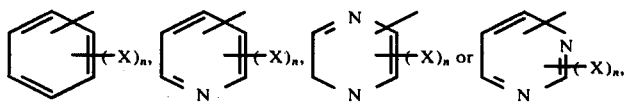

wherein:
n is 0, 1, 2 or 3; and
X is nitro, cyano, halo (fluoro, chloro, bromo and iodo, inclusive), lower aklyl, lower alkoxy, lower alkylthio or lower alkylsulfinyl, with the proviso that R does not bear more than one nitro group, lower alkylthio group or lower alkylsulfinyl group.
By "lower alkyl" is meant in all instances alkyl of 1 to 4 carbon atoms (i.e. methyl, ethyl, propyl and butyl).

SUMMARY OF THE INVENTION

We have discovered that mixtures of (1) a quaternary ammonium salt(s) and (2) 1,4-diazabicyclo[2.2.2]-octane

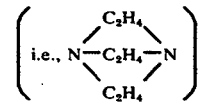

are novel catalysts in the process comprising reacting by contacting (a) an alkali metal phenate, pyridinate or pyrimidinate with (b) an O,O-dialkyl phosphorochloridothioate or an O-alkyl phenylphosphonochloridothioate to produce the corresponding phosphorothioates and phenylphosphonothioates. Our novel two-component catalyst represents a substantial process improvement over the prior art in that the reaction rate is higher and the desired products are obtained in extremely high yields and purity.

Essentially any compound from the known class of quaternary ammonium compounds can be used in the instant invention. Suitable quaternary ammonium salts have a minimum solubility of at least about 1 weight percent in the liquid reaction medium at 25° C, and in the case of a 2-phase reaction medium described below, suitable salts have a minimum solubility of at least about 1 weight percent in both the organic phase and the aqueous phase at 25° C. The ammonium salts can be represented by the formula $R_1'R_2'R_3'R_4'N^+A^-$ (VI), wherein $R_1'$–$R_4'$ are hydrocarbyl groups (e.g., alkyl, aryl, alkaryl, aralkyl, cycloalkyl, etc.) and $R_1'$ can join with $R_2'$ to form a 5- or 6-membered heterocyclic compound having at least one quaternized nitrogen atom in the ring and may also contain one atom of nitrogen, oxygen or sulfur within the ring. Typically, $R_1'-R_4'$ are hydrocarbyl groups of from 1 to about 12 carbon atoms. $A^-$ is a neutralizing anion and may be varied to convenience. Chloride and bromide are the preferred anions, but other illustrated anions include fluoride, iodide, tosylate, acetate, bisulfate, etc. The following compounds are illustrative: tetra-alkyl ammonium salts, such as tetramethyl-, tetraethyl-, tetrabutyl-, tetrahexyl-, methyltriethyl-, and trioctylmethyl- and tridecylmethyl-ammonium chlorides, bromides, iodides, bisulfates, tosylates, etc.; aralkylammonium salts, such as tetrabenzylammonium chloride, benzyltrimethyl-, benzyltriethyl-, benzyltributyl-, and phenethyltrimethyl-ammonium chlorides, bromides, iodides, etc.; arylammonium salts, such as triphenylmethylammonium fluoride, chloride or bromide, N,N,N-trimethylanilinium chloride, N,N,N-triethylanilinium bromide, N,N-diethyl-N-ethylanilinium bisulfate, trimethylnaphthylammonium chloride, p-methylphenyltrimethylammonium chloride or tosylate, etc.; five- and six-membered heterocyclic compounds containing at least one quaternized nitrogen atom in the ring, such as N,N,N',N'-tetramethylpiperazinium dichloride, N-methylpyridinium chloride, N-hexylpyridinium iodide, 4-pyridyltrimethylammonium iodide, 1-methyl-1-azoniabicyclo[2.2.1]heptane bromide, N,N-dibutylmorpholinium chloride, N-ethylthiazolium chloride, N-butylpyrrolium chloride, etc., and other like compounds.

The preferred catalyst system is a mixture of (1) benzyltrimethylammonium chloride (or bromide) or benzyltriethylammonium chloride (or bromide) and (2) 1,4-diazabicyclo[2.2.2]octane, hereafter triethylenediamine. The most preferred catalyst system is a mixture of benzyltriethylammonium chloride and triethylenediamine.

The mole ratio of (1) to (2) can vary from about 1:20 to 20:1, but a mole ratio of about 1:2 to 2:1 is preferred in most instances.

The mixtures of (1) and (2) are used in the process in small but catalytic amounts. For example, amounts from about 0.25 to about 20 mole percent, based on the reactants, are suitable but amounts of from about 0.5 to about 2 mole percent are generally preferred.

The reaction proceeds at a satisfactory rate at temperatures of from about 0° C. up to about 100° C. with a preferred rate being obtained at temperatures of about 40°–60° C. The reaction pressure is not critical and generally atmospheric or superatmospheric pressures are used as a matter of convenience. Under the above conditions, reaction times of up to 8 hours are common although reaction times of from 0.25 to 5 hours are generally sufficient for the reaction to be substantially complete.

The process is typically conducted in a liquid reaction medium as a convenient means of controlling the reaction temperature. The solvent may be an inert organic liquid such as methylene chloride ($CH_2Cl_2$), chloroform, carbon tetrachloride, benzene, toluene, cyclohexane, and other like chlorinated hydrocarbon solvents and hydrocarbon solvents. Alternatively, the process can be conducted in a two-phase solvent system comprising an inert, water-immiscible, organic liquid and water. The two-phase system is currently preferred because the by-product chloride is washed free from the reaction and is retained in the aqueous phase while the product is retained in the organic phase. A liquid mixture of methylene chloride and water represents the most preferred solvent mixture. The discovery that the process could be conducted in the presence of water without deleteriously affecting the product yield, etc., was most surprising since the phosphorochloridothioates and phenylphosphonochloridothioates are known to decompose in water. Furthermore, the alkali metal phenates, pyridinates and pyrimidinates have an inverse water-solubility as compared to the phosphorochloridothioates and phenylphosphonochloridothioates. The use of a two-phase solvent system would, therefore, be expected to slow the reaction by virtue of the fact that one reactant would be in the aqueous phase and the other reactant would be in the organic phase and contact between the two reactants would, therefore, be lessened.

The process is conducted under alkaline conditions. Generally the pH of the water phase (when present) is in the range of from about 7 to about 13. Such conditions can be easily achieved by conventional methods, e.g., by conducting the process in the presence of caustic, or other base or by use of an appropriate buffer system.

Agitation (e.g., stirring, swirling, etc.) of the reaction mixture is advantageous, particularly when the process is conducted in the 2-phase liquid reaction medium.

The Reactants

The alkali metal phenates, pyridinates and pyrimidinates are known classes of compounds corresponding to the formulas

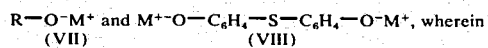

$$R-O^-M^+ \text{ and } M^{+-}O-C_6H_4-S-C_6H_4-O^-M^+, \text{ wherein}$$
$$(VII) \qquad\qquad\qquad (VIII)$$

wherein

R has the above meaning and M is an alkali metal (Li, Na, K, etc.) but is preferably sodium or potassium and is most preferably sodium.

The O,O-dialkyl phosphorochloridothioates and O-alkyl phenylphosphonochloridothioates are likewise well known classes of compounds which correspond to the formulas

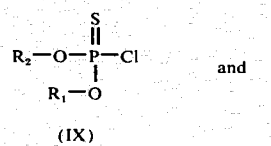 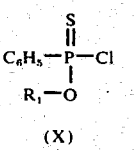

wherein $R_1$ and $R_2$ are each independently lower alkyl but are preferably methyl or ethyl.

Various phosphorothioates and phenylphosphonothioates can obviously be prepared by using various combinations of the above reactants. Representative and illustrative lists of suitable reactants and combinations thereof are shown in Tables 1 and 2 below:

Table 1

$$R_2-O-\underset{\underset{O-R_1}{|}}{\overset{\overset{S}{\|}}{P}}-Cl + R-O^-M^+ \longrightarrow R-O-\underset{\underset{O-R_1}{|}}{\overset{\overset{S}{\|}}{P}}-O-R_2$$

| No. | R₁ | R₂ | R | M |
|---|---|---|---|---|
| 1 | CH₃ | CH₃ | 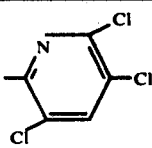 3,5,6-trichloropyridin-2-yl | Na |
| 2 | C₂H₅ | C₂H₅ | 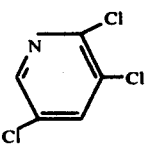 3,5-dichloropyridin-2-yl | Na |
| 3 | C₂H₅ | C₂H₅ | 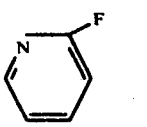 2-fluoropyridin-3-yl | Na |
| 4 | CH₃ | CH₃ | 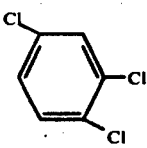 2,4,5-trichlorophenyl | Na |
| 5 | C₂H₅ | C₂H₅ | 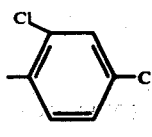 2,4-dichlorophenyl | K |
| 6 | CH₃ | CH₃ | 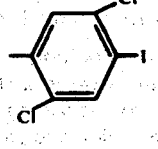 2,5-dichloro-4-iodophenyl | Na |
| 7 | CH₃ | CH₃ | 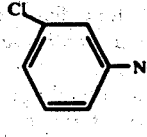 2-chloro-4-nitrophenyl | Na |
| 8 | C₂H₅ | C₂H₅ | 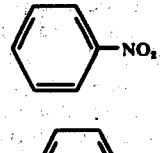 4-nitrophenyl | Na |
| 9 | CH₃ | CH₃ | 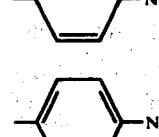 4-nitrophenyl | K |
| 10 | CH₃ | CH₃ | 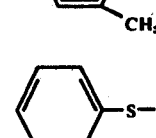 3-methyl-4-nitrophenyl | K |
| 11 | CH₃ | CH₃ | 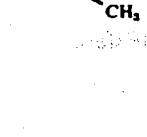 3-methyl-2-(methylthio)pyridinyl | Na |

Table 1-continued $$R_2-O-\overset{\overset{S}{\|}}{\underset{\underset{R_1-O}{|}}{P}}-Cl + R-O^-M^+ \longrightarrow R-O-\overset{\overset{S}{\|}}{\underset{\underset{O-R_1}{|}}{P}}-O-R_2$$

| No. | R₁ | R₂ | R | M |
|---|---|---|---|---|
| 12 | C₂H₅ | C₂H₅ | ![phenyl with S(O)CH₃ and CH₃] | Na |
| 13 | C₂H₅ | C₂H₅ | ![phenyl with S(O)CH₃] | Na |
| 14 | C₂H₅ | C₂H₅ | ![pyrazine with CH(CH₃)₂] | K |
| 15 | C₂H₅ | C₂H₅ | ![pyrazine] | Na |
| 16 | CH₃ | CH₃ | ![phenyl-CN] | K |

Table 2

$$C_6H_5-\overset{\overset{S}{\|}}{\underset{\underset{R_1-O}{|}}{P}}-Cl + R-O^-M^+ \longrightarrow R-O-\overset{\overset{S}{\|}}{\underset{\underset{O-R_1}{|}}{P}}-C_6H_5$$

| No. | R₁ | R | M |
|---|---|---|---|
| 17 | CH₃ | ![phenyl with Cl, Br, Cl] | Na |
| 18 | C₂H₅ | ![phenyl-NO₂] | K |
| 19 | C₂H₅ | ![phenyl-CN] | Na |

The compounds of formula (V) are prepared in like manner.

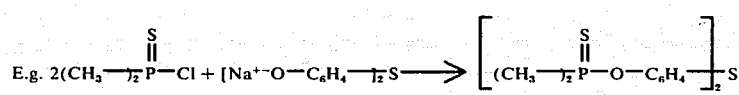

E.g. $2(CH_3\!-\!)_2\overset{\overset{S}{\|}}{P}\!-\!Cl + [Na^+\!-\!O\!-\!C_6H_4\!-\!]_2S \longrightarrow [(CH_3\!-\!)_2\overset{\overset{S}{\|}}{P}\!-\!O\!-\!C_6H_4\!-\!]_2S$ The following examples further illustrate the invention.

EXAMPLE 1

Preparation of O,O-Diethyl O-3,5,6-Trichloro-2-Pyridyl Phosphorothioate

O,O-Diethyl phosphorochloridothioate (11.3 g., 0.06 mole) was added dropwise to a stirred mixture of (1) sodium 3,5,6-trichloro-2-pyridinate (13.2 g., .06 mole) in 30 ml. of methylene chloride and 74 ml. of water, (2) 1 mole percent triethylene diamine, (3) 1 mole percent benzyltriethylammonium chloride and (4) a pH buffer consisting of NaOH and sodium borate. The stirred reaction mixture was maintained at 42° C. for 1.5 hours, cooled to room temperature, and the organic phase separated from the aqueous phase. The organic phase was washed once with approximately 30 ml. water and the organic solvent removed under reduced pressure. The title compound was thus obtained in 97 percent yield, based on 100 percent conversion of starting materials. The product was of excellent purity (approximately 99% pure).

EXAMPLES 2–3

The following examples were run under essentially the same procedure, reactants and process conditions as Example 1 except for the catalyst system and reaction times. Results were:

| Ex. | Co-Catalyst | Mole % | Reaction Time (Hrs.) | Percent Yield |
|---|---|---|---|---|
| 2 | $C_6H_5$—$N^+$—$(CH_3)_3Cl^-$ Triethylenediamine | 2 2 | 5.1 | 94 |
| 3 | Cl—$CH_2$—N⁺⟨⟩N Cl⁻ Triethylenediamine | 1 1 | 17.75 | 97 |

The products of Examples 2 and 3 were likewise obtained in excellent purity.

Examples 4-5

| Example | Reactants | Product |
|---|---|---|
| 4 | DEPCT + Na⁺⁻O—⟨C₆H₄⟩—NO₂ → | $(C_2H_5O{-})_2 P(S)$—O—⟨C₆H₄⟩—NO₂ |
| 5 | DEPCT + Na⁺⁻O—⟨C₆H₃Cl⟩—Cl → | $(C_2H_5O{-})_2 P(S)$—O—⟨C₆H₃Cl⟩—Cl |

In this series of experiments the procedure and process conditions were substantially the same as in Example 1. However, here the reaction time was 3–4 hours and no boric acid was included in the reaction mixture. Additionally, the catalyst level was lowered to 0.75 mole percent of triethylenediamine and 0.75 mole percent of benzyltriethylammonium chloride, based on combined starting materials. The products from Examples 4 and 5 were obtained in 92.1 and 93.1 percent yields, respectively.

Other products can be similarly prepared by appropriate choice of reactants and by using the same catalyst systems as in Examples 1–5 or by use of other catalyst mixtures as defined above.

We claim:

1. In the process of preparing a compound corresponding to the formula $$R-O-\underset{\underset{O-R_1}{|}}{\overset{\overset{S}{\|}}{P}}-O-R_2, \quad R-O-\underset{\underset{O-R_1}{|}}{\overset{\overset{S}{\|}}{P}}-C_6H_5 \text{ or}$$

$$R_2-O-\underset{\underset{R_1-O}{|}}{\overset{\overset{S}{\|}}{P}}-O-C_6H_4-S-C_6H_4-O-\underset{\underset{O-R_1}{|}}{\overset{\overset{S}{\|}}{P}}-O-R_2,$$

wherein:

$R_1$ and $R_2$ are each independently lower alkyl; and R is

[benzene ring with $(X)_n$ substituent]

wherein:

n is 0, 1, 2 or 3; and

X is nitro, cyano, halo, lower alkyl, lower alkoxy, lower alkylthio or lower alkylsulfinyl, with the proviso that R does not bear more than one nitro group, lower alkylthio group or lower alkylsulfinyl group;

by reacting in an inert liquid reaction medium under neutral or alkaline conditions (a) a compound corresponding to the formula $$R-O^-M^+$$

or $$M^+O^-—C_6H_4—S—C_6H_4—O^-M^+$$

with (b) a compound corresponding to the formula $$R_2-O-\underset{\underset{R_1-O}{|}}{\overset{\overset{S}{\|}}{P}}-Cl \text{ or } C_6H_5-\underset{\underset{R_1-O}{|}}{\overset{\overset{S}{\|}}{P}}-Cl$$

wherein M is an alkali metal and R, $R_1$ and $R_2$ have the aforesaid meaning;

the improvement consisting of conducting the process in the presence of a small but catalytic amount of (1) a quaternary ammonium salt having a minimum solubility of at least 1 weight percent in the liquid reaction medium at 25° C and (2) 1,4-diazabicyclo[2.2.2]octane.

2. The process defined in claim 1 wherein (1) is a quaternary ammonium salt of the formula $R_1'R_2'R_3'R_4'N^+A^-$, wherein $R_1'$–$R_4'$ are each independently hydrocarbyl groups of from 1 to about 12 carbon atoms, or $R_1'$ is joined with $R_2'$ to form a 5- or 6-membered heterocyclic ring wherein one member of said heterocyclic ring is a quaternized nitrogen atom, a second member of said heterocyclic ring is an atom of carbon, or a nonadjacent atom of nitrogen, oxygen or sulfur, and the remaining members of said heterocyclic ring are carbon atoms; and $A^-$ is a neutralizing anion; said quaternary ammonium salt having a maximum carbon content of about 31 carbon atoms.

3. The process defined in claim 2 wherein (1) is benzyltrimethylammonium chloride or bromide, or benzyltriethylammonium chloride or bromide.

4. The process defined in claim 3 wherein (1) is benzyltriethylammonium chloride.

5. The process defined in claim 1 wherein the mole ratio of (1) to (2) is from about 1:20 to about 20:1.

6. The process defined in claim 5 wherein said ratio is from about 1:2 to about 2:1.

7. The process defined in claim 1 wherein the combined amount of (1) and (2) is from about 0.25 to about 20 mole percent, based on the combined moles of (a) and (b).

8. The process defined in claim 7 wherein the combined amount of (1) and (2) is from about 0.5 to about 2 mole percent.

9. The process defined in claim 1 wherein said process is conducted in an agitated two-phase solvent system consisting of an inert water-immiscible organic liquid and water.

10. The process defined in claim 1 wherein $R_1$ and $R_2$ are methyl or ethyl.

11. The process defined in claim 1 wherein R is

12. The process defined by claim 11 wherein (1) is benzyltrimethylammonium chloride or bromide or benzyltriethylammonium chloride or bromide.

13. The process defined in claim 12 wherein (2) is benzyltriethylammonium chloride.

14. The process defined in claim 13 wherein said process is conducted in an agitated two-phase solvent system consisting of an inert water-immiscible organic liquid and water.

15. The process defined in claim 14 wherein (a) is sodium 4-nitrophenate or 2,4-dichlorophenate and (b) is O,O-diethyl phosphorochloridothioate; said two-phase solvent system is a mixture of methylene chloride and water; and the reaction temperature is from about 40° to about 60° C.

* * * * *

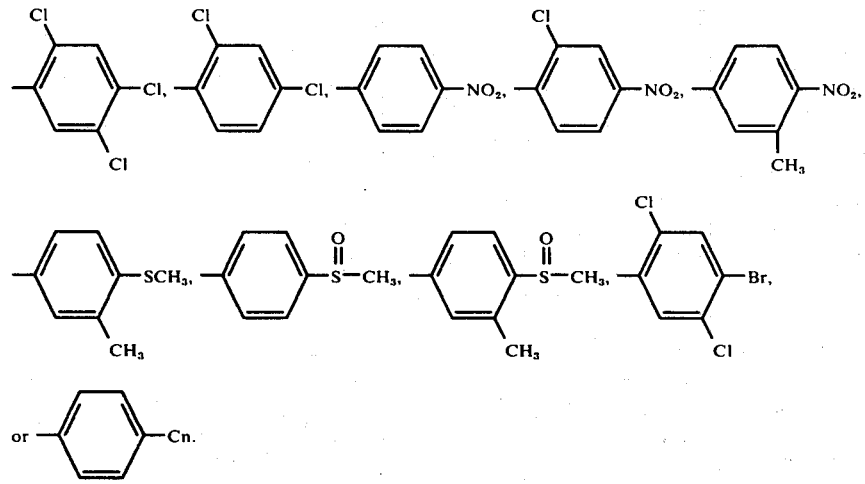

UNITED STATES PATENT OFFICE
CERTIFICATE OF CORRECTION

Patent No. 4,016,225          Dated April 5, 1977

Inventor(s) Lorraine M. Kroposki et al.

It is certified that error appears in the above-identified patent and that said Letters Patent are hereby corrected as shown below:

Title page, column 2, line 7: "pyrimidiate" should read --pyrimidinate--.

Column 2, line 12: "$R_2-O-\overset{S}{\underset{R_1-O}{\overset{\|}{P}}}-O-C_6H_4-S-C_6H_5-O-\overset{S}{\underset{O-R_1}{\overset{\|}{P}}}-O-R_2$" should read
(V)

$--R_2-O-\overset{S}{\underset{R_1-O}{\overset{\|}{P}}}-O-C_6H_4-S-C_6H_4-O-\overset{S}{\underset{O-R_1}{\overset{\|}{P}}}-O-R_2--.$
(V)

Column 4, line 42: "$R-O^-M^+$ and $M^{+-}O-C_6H_4-S-C_6H_4-O^-M^+$, wherein"
              (VII)              (VIII)

should read $--R-O^{\ominus}M^{\oplus}$ and $M^{\oplus\ominus}O-C_6H_4-S-C_6H_4-O^{\ominus}M^{\oplus},--.$
        (VII)            (VIII)

Column 5, lines 5, 6, 7, 10, 11 and 14 and Col. 7, lines 6 and 7: The benzene rings should have a bond extending from the middle left point toward the left.

Column 7, line 60:
"E.g. $2(CH_3)_2\overset{S}{\overset{\|}{P}}-Cl + [Na^{+-}O-C_6H_4]_2S \longrightarrow [(CH_3)_2\overset{S}{\overset{\|}{P}}-O-C_6H_4]_2S$" should read --E.g. $2(CH_3O)_2\overset{S}{\overset{\|}{P}}-Cl + [Na^{\oplus\ominus}O-C_6H_4]_2S \longrightarrow [(CH_3O)_2\overset{S}{\overset{\|}{P}}-O-C_6H_4]_2S--$

UNITED STATES PATENT OFFICE
CERTIFICATE OF CORRECTION

Patent No. 4,016,225          Dated April 5, 1977

Inventor(s) Lorraine M. Kroposki et al.

It is certified that error appears in the above-identified patent and that said Letters Patent are hereby corrected as shown below:

Column 9, lines 12 and 13, in the formulas across from Examples 4 and 5:  All four hexagonal rings should have a circle in the middle of each to denote a benzene ring.

Column 9, line 29: Insert the footnote for Examples 4-5 which reads --"DEPCT" stands for O,O-diethylphosphorochloridothioate.--

Column 11, line 10: "Claim 1" should read --Claim 11--.

Column 11, line 30: "or ⌬Cn." should read --or ⌬-CN.--.

Signed and Sealed this twenty-third Day of August 1977

[SEAL]

Attest:

RUTH C. MASON
*Attesting Officer*

C. MARSHALL DANN
*Commissioner of Patents and Trademarks*